(12) United States Patent
Minn et al.

(10) Patent No.: US 8,674,680 B2
(45) Date of Patent: Mar. 18, 2014

(54) METHOD AND DEVICE FOR FAST MEASUREMENT OF FREQUENCY RESPONSE WITH SCALABLE SHORT CHIRP SIGNALS

(75) Inventors: Mart Minn, Tallinn (EE); Toivo Paavle, Tallinn (EE); Raul Land, Tallinn (EE); Paul Annus, Tallinn (EE); Toomas Parve, Tallinn (EE)

(73) Assignee: Tallinn University of Technology OÜ Eliko Tehnoloogia Arenduskeskus, Tallinn (EE)

( * ) Notice: Subject to any disclaimer, the term of this patent is extended or adjusted under 35 U.S.C. 154(b) by 560 days.

(21) Appl. No.: 12/911,432

(22) Filed: Oct. 25, 2010

(65) Prior Publication Data

US 2011/0095747 A1    Apr. 28, 2011

(30) Foreign Application Priority Data

Oct. 23, 2009  (EP) ..................................... 09013404

(51) Int. Cl.
*G01R 23/02*       (2006.01)

(52) U.S. Cl.
USPC .................. 324/76.39; 324/76.11; 324/76.12; 324/76.21; 702/75; 702/76; 702/77

(58) Field of Classification Search
USPC ........ 324/76.11, 76.12, 76.21, 76.39; 702/75, 702/76, 77
See application file for complete search history.

(56) References Cited

U.S. PATENT DOCUMENTS

| | | | | |
|---|---|---|---|---|
| 6,154,375 A | * | 11/2000 | Majid et al. | 363/16 |
| 6,317,696 B1 | * | 11/2001 | Clements et al. | 702/50 |
| 6,916,656 B2 | * | 7/2005 | Walters et al. | 435/450 |
| 2006/0100539 A1 | * | 5/2006 | Min et al. | 600/547 |

FOREIGN PATENT DOCUMENTS

WO    2009096821 A1    8/2009

OTHER PUBLICATIONS

Paavle, Toivo, Min, Mart, and Parve, Toomas, Using of Chirp Excitation for Bioimpedance Estimation:Theoretical Aspects and Modeling, Oct. 6, 2008, ALL.*
Paavle et al. Wideband Object Indentification with Rectangular Wave Chirp Excitation, Aug. 23, 2009, ALL.*
Nahvi, M. and Hoyle, B.S, Electrical Impedance Spectroscopy Sensing for Industrial Processes. Dec. 2009, vol. 9, No. 12., ALL.*
Nahvi, M and Hoyle, B.S., Wideband electrical impedance tomography, Jul. 24, 2008, ALL.*
Paavle, Toivo, Min, Mart, and Parve, Toomas, Using of Chirp Excitation for Bioimpedance Estimation: Theoretical Aspects and Modeling, Oct. 6, 2008, ALL.*

(Continued)

*Primary Examiner* — Patrick Assouad
*Assistant Examiner* — Sean Curtis
(74) *Attorney, Agent, or Firm* — Maine Cernota & Rardin

(57) ABSTRACT

A method and device are provided for fast impedance measurement of a biological object having dynamically varying in time parameters, wherein a titlet shaped pulse is introduced into the object and a voltage response signal is measured and analyzed by a processing unit for estimating the impedance of the object. The titlet pulse has a start frequency substantially in one end of the frequency range of interest and a stop frequency substantially in the other end of the frequency range of interest and a duration of the titlet pulse is one cycle or less.

19 Claims, 11 Drawing Sheets

(56) References Cited

OTHER PUBLICATIONS

Min et al. Broadband excitation for short-time impedance spectroscopy, Nov. 30, 2007, ALL.*

Paavle et al. Wideband Object Identification with Rectangular Wave Chirp Excitation, Aug. 23, 2009, ALL.*

EP Search Report for EP Application No. 09013404, filed on Oct. 23, 2009, 2 pages.

Paavle, T. et al., "Using of Chirp Excitation for Bioimpedance Estimation: Theoretical Aspects and Modeling", Electronics Conference, 2008, pp. 325-328.

Paavle, T. et al., "Wideband Object Identification With Rectangular Wave Chirp Excitation", Circuit Theory and Design, 2009, pp. 421-424.

Paavle, T. et al., "Bioimpedance Monitoring with Improved Accuracy Using Three-Level Stimulus", Circuit Theory and Design, 2007, pp. 412-415.

* cited by examiner

METHOD AND DEVICE FOR FAST MEASUREMENT OF FREQUENCY RESPONSE WITH SCALABLE SHORT CHIRP SIGNALS

RELATED APPLICATIONS

This application claims the benefit of European Application No. 09013404.0, filed Oct. 23, 2009. This application is herein incorporated by reference in its entirety for all purposes.

FIELD OF THE INVENTION

The invention belongs to the field of measuring frequency dependent properties of an object, such as biological object.

BACKGROUND OF THE INVENTION

Using sine wave excitation and frequency domain measurements, such as bioimpedance measurements is common approach in assessing passive electrical properties of different objects, such as biological object. However, frequency sweeping or hopping of a sine wave excitation over a wide frequency range is too slow for performing impedance spectroscopy to recover fast impedance changes in biological objects such as caused by single cells and cell cultures in high throughput microfluidic devices (lab-on-a-chip type analyzers and micro-reactors). The use of short-time and broad frequency band single-pulse excitation and monitoring the response as a function of time is informative and will greatly reduce the measurement interval (Pliquett et al., 2000).

Chirp signals, i.e. multi-cycle sine wave based signals in which the frequency increases ('up-chirp') or decreases ('down-chirp') continuously as a function of time, are widely used in radar and sonar applications, acoustic, ultrasonic, optical and seismological studies (Pollakowski and Ermert, 1995; Müller and Massarani, 2001; Misairidis and Jensen, 2005; Rufer et al., 2005). The main advantage of chirp signals is their well defined frequency range (from start to stop frequency of the chirp) and constant or accurately predetermined power spectral density, PSD, for wide range of frequencies, also acceptable crest factor and signal-to-noise ratio (Müller and Massarini, 2001; Misairidis and Jensen, 2005). Recently, using of chirp and modified (e.g. windowed) chirp signals is proposed for estimation of the frequency response of electrical impedance (the impedance spectrum), particularly of biological objects (Min et al., 2007a; Paavle et al., 2008 and 2009; Nahvi and Hoyle, 2008 and 2009; Hoyle and Nahvi, 2008). Suitable signal processing methods are introduced by Vaseghi, 2006 and Chu, 2008.

Using of rectangular chirps is also known (Pollakowski and Ermert, 1994; Rufeert et al., 2005). Signal processing is much simpler for rectangular wave excitation with only constant binary values, +A, and −A. Moreover, the rectangular waveforms have the minimally possible unity value crest factor (ratio of a peak value to a root-mean-square level). A widely used method is to generate a pseudo-random maximum length sequence (MLS) of rectangular signals (Sun et al., 2007a 2007b 2009; Gawad et al., 2007). Also, rectangular chirp signal which can be described as a signum-chirp function instead of the classical sinusoidal chirp is proposed. Besides the simplest rectangular chirp having non-return-to-zero (NRZ) pulses (binary chirp, zero-states are absent), some versions of return-to-zero (RZ) rectangular pulse chirp function (ternary chirp, +A; 0; −A values) have been suggested for excitation waveforms (Min et al., 2007b, 2009b, 2009c; Paavle et al., 2009, 2010). Using of chirp signals (both, based on sine wave and rectangular wave) have several advantages, including short excitation and measurement time and well determined excitation bandwidth (frequency range), so that the most of generated energy (85 to 99%) is concentrated into the useful bandwidth, and constant level or otherwise specified power spectral density (PSD) within the useful bandwidth (Min et al, 2009a). This is true, if the number of cycles in chirp is minimally about 100, and will be exact, if the number of cycles is 100,000 and higher. At a low number of cycles the spectrum becomes significantly distorted. The distortions become very large, if the number of cycles goes lower than 10.

However, the spectroscopy of dynamic objects with rapidly changing impedances is still challenging as it is commonly assumed that chirps contain hundreds, thousands, and even millions of signal cycles at high frequencies. Very fast changing impedances, as in the case of moving objects as bacteria, cells, droplets, bubbles, etc. in microfluidic devices, require a very short excitation time to avoid the dynamic errors of spectrogram (primarily of the timeline sequence of spectral snapshots) due to the quick changes. Another similar example is the pulsating impedance of the cardiovascular system of living organisms.

What is needed, therefore, is a fast measurement method scalable in both time and frequency domain for flexible performing of impedance spectroscopy of dynamic impedances.

What is also needed is that as much as possible energy of the signal is generated within the excitation bandwidth to minimize the power consumption, getting better signal-to-noise ratio, and avoiding the heating or other unwanted effects on the object due to out-of-bandwidth components of the excitation signal.

SUMMARY OF THE INVENTION

Various embodiments of the present invention are based on a notion that certain short pulses formed similarly to a chirp signal, i.e., as a sinusoidal or rectangular function of constantly increasing or decreasing frequency over time from start frequency to stop frequency, but pulse having only one cycle or less (e.g. 0.5 and 0.25) obtain new properties in comparison with traditional multi-cycle chirp signals. In principal, such the very short pulses are not chirp signals but are related to. Such chirp-like pulses, or titlets, have surprisingly effective properties in terms of controllable duration, power spectral density, and bandwidth.

The goal of one embodiment of the invention is to introduce using titlets, where frequency response from an object must be obtained during very short measurement interval. For example, to use titlets containing only p=1, 0.5 or 0.25 cycles instead of multi-cycle chirps, where p is a number of cycles used.

According to further embodiments of the invention, the frequency of the titlet is changed up-wards or down-wards (i.e., starting from the start frequency and increased until the stop frequency, or starting from the start frequency and decreased until the stop frequency) according to any suitable function of time F(t), including a linear one, F(t)=at. However, according to preferred embodiment, the frequency is changed according to an exponential function $m^t$, or according to power law $t^m$, or logarithmic law $\log_m t$, where t is time and m is an arbitrary number, which can be also fractional. Moreover, the function F(t) can have not only analytical form, but can represent arbitrary dependence, e.g., in tabulated form.

According to further embodiments of the invention, amplitude of the titlet signal is also modified (modulated or windowed) in time by suitable functions, e.g. trigonometric or exponential ones. According to one embodiment, the amplitude is increased according to power function $t^n$, wherein n is selected large enough to equalize the power spectral density at lower frequencies, e.g., from around 2 to 10 for most cases.

Another embodiment of the invention is to generate two or more titlets as described above sequentially in time. A simple but effective case is generating of two 0.25 cycle titlets sequentially. For example, we can generate a double titlet signal in which the first titlet has up-wards running, and the other one down-wards running frequency. The excitation energy of such the combined double titlet pulse is higher than simply a doubled value of individual titlets because of better direction of the generated energy into the useful frequency bandwidth, or in other words, the shaping of spectrum is more effective. Different combinations of titlet sequences can be designed. For example, the sequence of two one-cycle titlets is a useful solution with highly concentrated energy (near to 90%) in the measurement bandwidth. In principal, double, triple, etc. different combinational titlet pulses can be designed for shaping the power spectrum in a manner suitable for a particular measurement task.

Another goal of some embodiments of invention is to provide energy efficient excitation signals, e.g., at least about 85% of generated energy must be included to the measurement bandwidth.

According to one embodiment of the invention, rectangular titlet pulses, both non-return-to-zero (binary, or two-level) and return-to-zero (ternary, or three-level) are generated. Particularly energy efficient are return-to-zero type ternary (three-level) titlets. Such signals have a duration of the zero state sections is from 15 to 30 degrees, preferably from 21 degrees to 22.5 degrees, most preferably 21.2 degrees.

According to one aspect of the invention, one full cycle rectangular titlet pulse signal is provided, where the duration of the cycle $T=2/f_2$ and the duration of the first half-cycle $T_1$ is $T/2^{1/2}$ and the duration of the second half-cycle $T_2$ is $T-T_1$. If the amplitudes during the first half-cycle and during the second half-cycle are equal, the signal includes DC component. To remove this component, the amplitudes of half-cycles are adjusted so that the areas of the signal in both half-cycles are equal, i.e., the amplitude of the second half-cycle is larger than for the first half-cycle.

Furthermore, the various embodiments of the invention allow building wideband scalable spectral analyzers where both excitation time and the frequency range can be set up and changed independently. This allows to conduct fast (but somewhat less accurate) and slower (but more accurate) measurements simply by changing the measurement time by choosing an appropriate number of cycles within the excitation titlet signal. For getting better signal-to-noise ratio, the measurement processes can be repeated in sequence.

The invention is, in one embodiment, best suited for wideband and short time spectroscopy of time variant (dynamic) impedances. The titlet signals allow scalability in both frequency and time domain, more than 85% of the generated energy falls into useful bandwidth and rectangular waveform allows reduce the complexity of impedance spectroscopy.

For modifying the spectral properties of excitation and/or increasing the signal-to-noise ratio, two or several individual titlets can be generated sequentially in time for forming a combinational titlet pulse.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Figure 17:
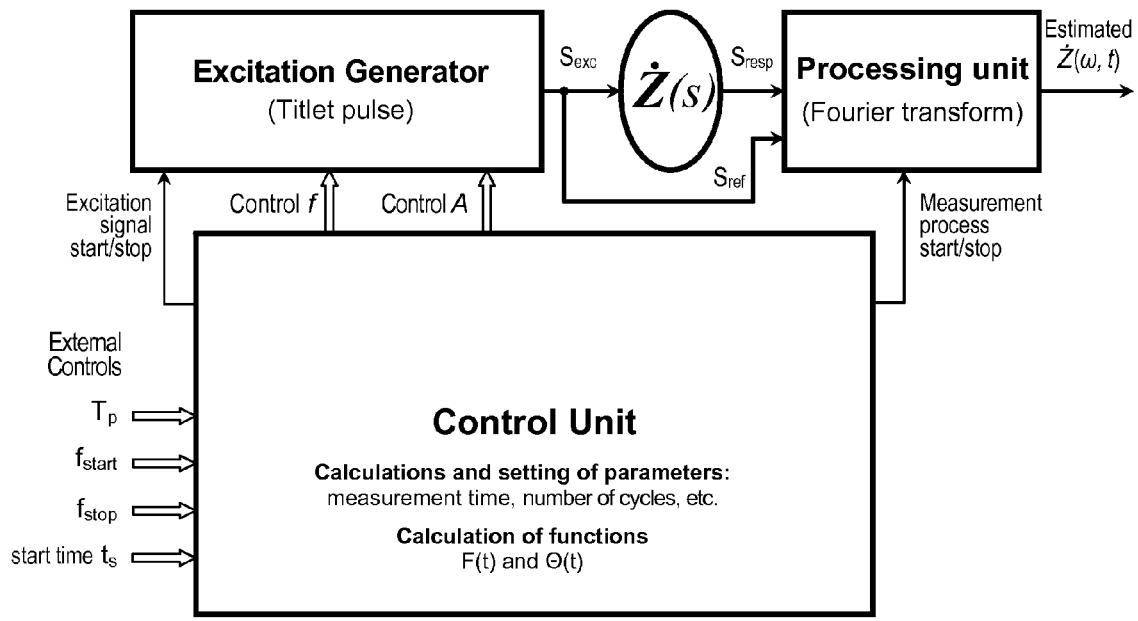
FIG. 17 is a generalized block diagram of a device for measurement of impedance spectrum using titlet excitation.

FIG. 17 describes a generalized architecture for a short time impedance spectroscopy system. Such the system contains an excitation generator and a processing unit for processing of the response signal from impedance under study Z, evoked as a result of excitation. Short time spectroscopy requires exact timing of excitation and processing procedures and control over frequency and amplitude of the short excitation pulses. Therefore a control unit with inputs for determining the starting time $t_s$, duration of excitation pulse $t_p$, and initial and final frequencies ($f_{start}$, $F_{stop}$) for excitation bandwidth B.

The control unit elaborates start/stop signals for both excitation and signal processing, and calculates the rules for changing frequency F(t) and phase θ(t). Processing unit performs Fourier transform and calculates frequency responses of the impedance Z.

There are three ways to find the frequency responses:
(a) to calculate first a cross-correlation function between excitation and response signals and then perform the Fourier transformation of the cross-correlation function as described in FIG. 18 and FIG. 20; or
(b) to perform the Fourier transformation of both response and excitation signals and then find the frequency response function calculating the ratio of these transformed signals; or
(c) to perform the Fourier transformation of the response signal and divide this by mathematical expression of the Fourier transformation of the known excitation signal, which is saved into a memory of the processing unit. In this case the excitation signal is required only as a reference for calculating the phase response function.

Figure 18:
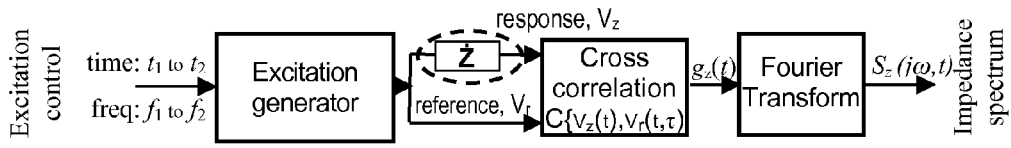
FIG. 18 is a simplified architecture of a fast and wideband impedance analyzer.

FIG. 18 depicts a simplified architecture of impedance analyzer, in which the excitation pulse (both chirp and titlet are applicable) is generated during the excitation time interval (duration of the excitation pulse Tp) from $t_1$ to $t_2$ for covering a pre-selected excitation bandwidth B from $f_1$ to $f_2$. The excitation signal is directed into the impedance under study Ż, and from the received response signal and said excitation signal the parameters and characteristic of the object (such as impedance) are calculated. For example, a deconvolution process is used, which results in obtaining the cross-correlation function, which represents the impulse response $g_z(t)$ of the complex impedance Ż. Performing the Fourier transform of $g_z(t)$, we receive a complex impedance spectrum $S_z(j\omega)$, from which we can separate the real and imaginary parts $Re\{Z(j\omega)\}$ and $Im\{Z(j\omega)\}$ or to calculate the frequency responses of magnitude $M_z(\omega)$ and phase $\theta_z(\omega)$.

The excitation signal generator is adjusted to generate excitation with required duration and with required start and stop frequencies. Such generators are known from the art.

Figure 1:
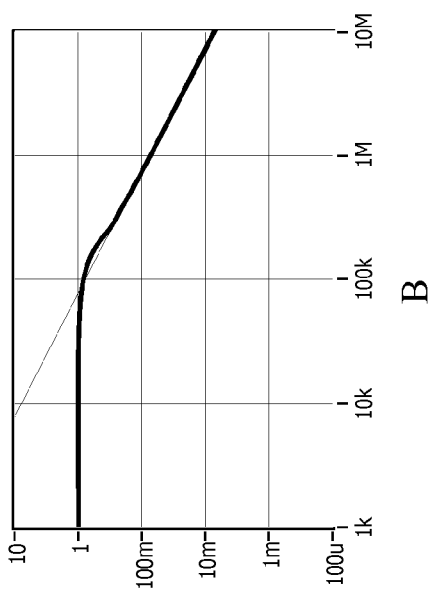
FIG. 1 is a 5 μs quarter cycle (p=¼) linear frequency titlet pulse having upper limit of the effective bandwidth $f_2=100$ kHz (A), and frequency distribution of its relative spectral density (B).
Figure 1:
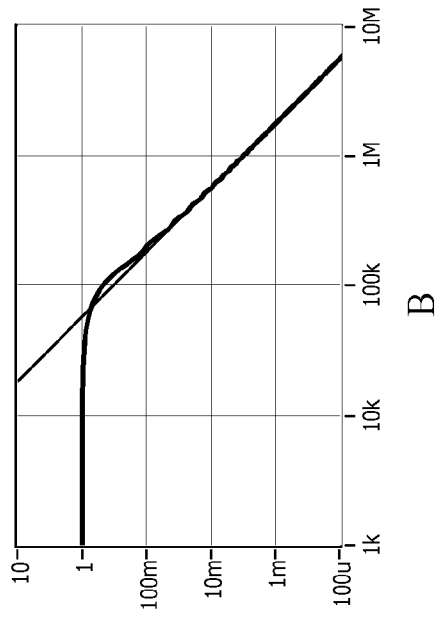
Figure 2:
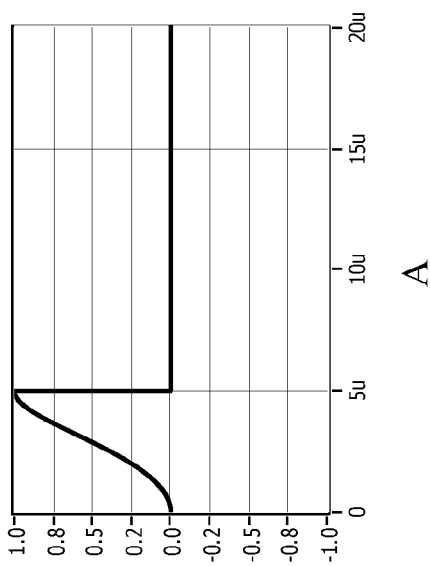
FIG. 2 is a 10 μs half cycle (p=½) linear frequency titlet pulse having upper effective bandwidth limit $f_2=100$ kHz (A), and frequency distribution of its relative spectral density (B).
Figure 2:
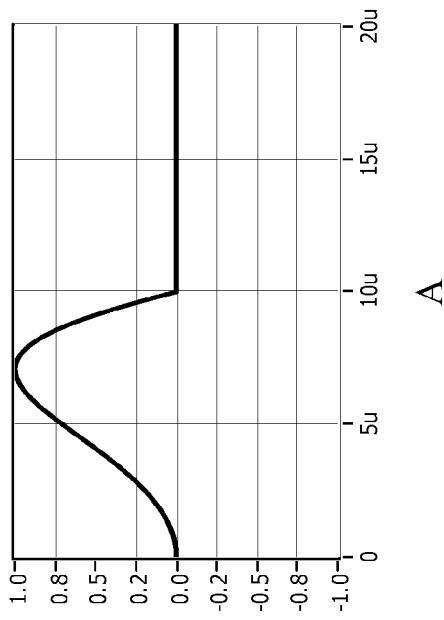
Figure 3:
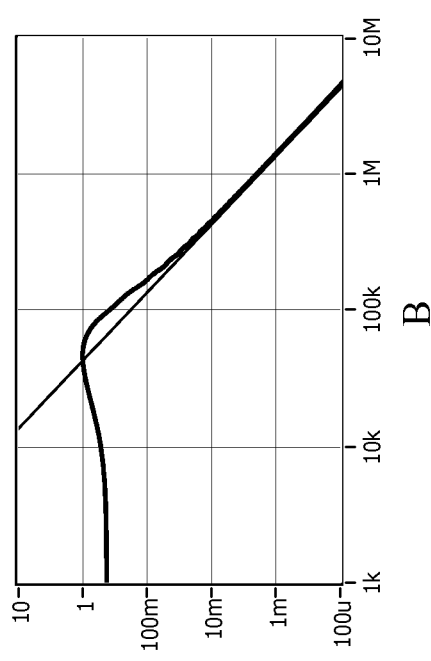
FIG. 3 is a 20 μs full cycle (p=1) linear frequency titlet pulse having upper effective bandwidth limit $f_2=100$ kHz (A), and frequency distribution of its relative spectral density (B).
Figure 3:
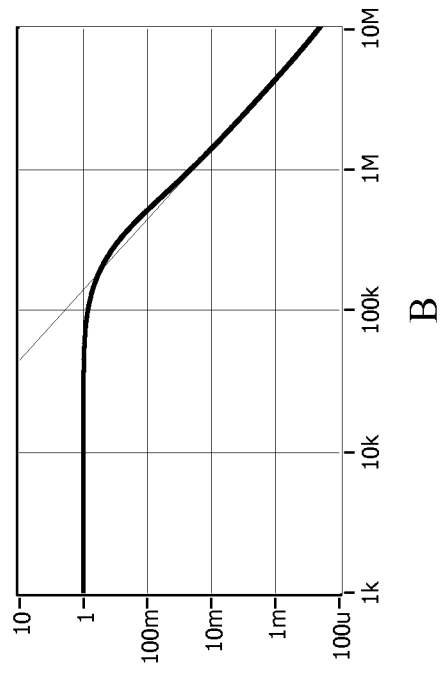
Figure 4:
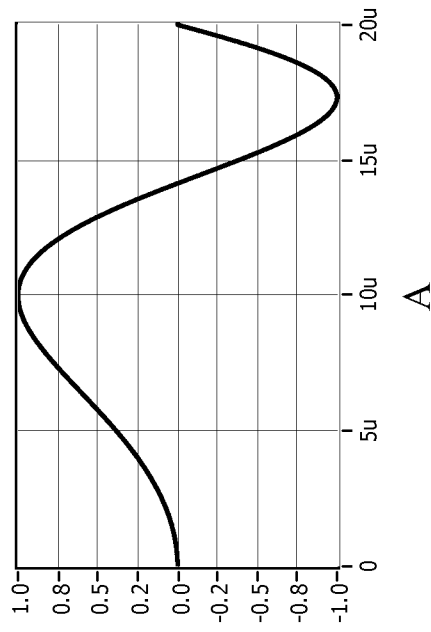
FIG. 4 is a 20 μs full cycle (p=1) exponential frequency titlet pulse having upper effective bandwidth limit $f_2=100$ kHz (A), and frequency distribution of its relative spectral density (B).
Figure 4:
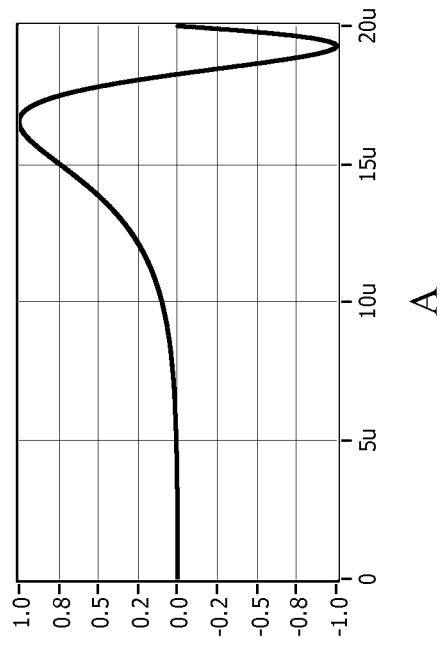
Figure 5:
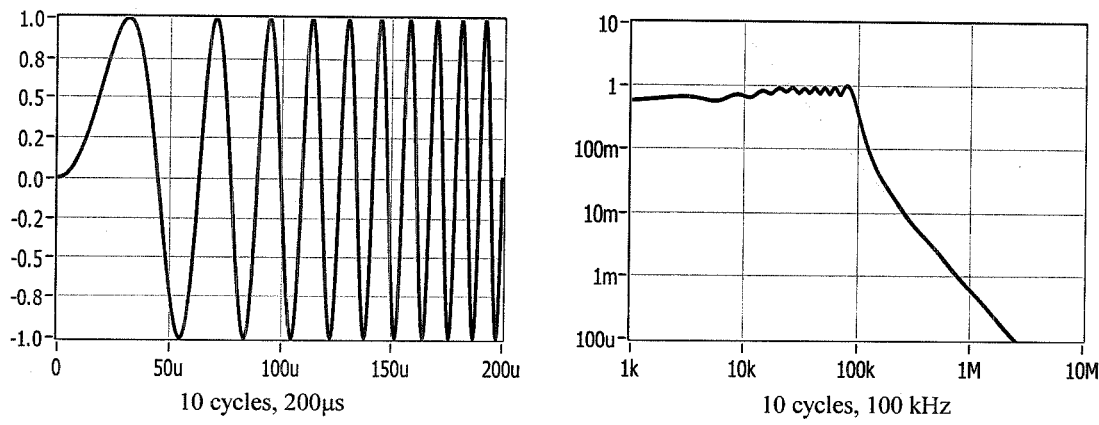
FIG. 5 shows a 200 μs 10-cycle (p=10) linear frequency chirp having upper limit of the effective bandwidth $f_2=100$ kHz (A), and frequency distribution of its relative spectral density (B).
Figure 6:
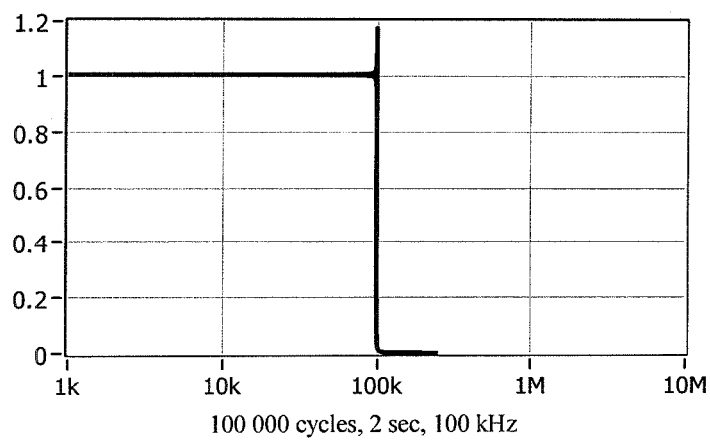
FIG. 6 is a frequency distribution of relative spectral density of the 100,000-cycle linear frequency chirp signal having upper limit of the effective bandwidth $f_2=100$ kHz; duration of the chirp is 2 sec.
Figure 7:
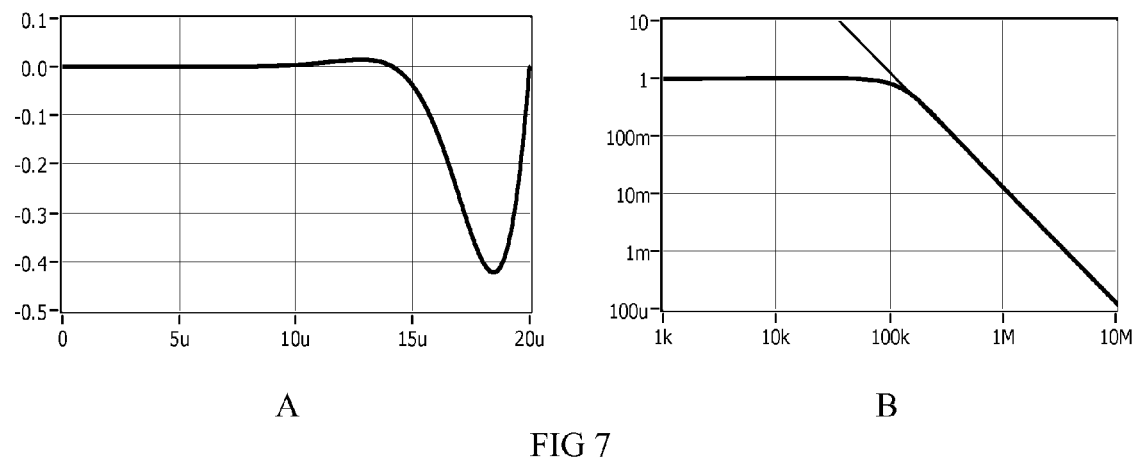
FIG. 7 is a 20 μs one cycle (p=1) linear frequency titlet pulse with amplitude control by the law of power of 8 having upper limit of the effective bandwidth $f_2=100$ kHz (A), and frequency distribution of its relative spectral density (B).

The chirp signals used in prior art are shown in FIG. 5A. Such signals have many, from tens to thousands and millions of cycles. Duration of the chirp (contains $10^5$ cycles) with almost ideal spectrum (flat spectral density function, 99.97% of energy within the useful bandwidth 100 kHz) in FIG. 6 is 2 seconds. Such the duration is too long for applications in dynamic spectroscopy. Spectral densities of the both chirp signals are shown in FIG. 5B and FIG. 6 correspondingly.

The titlet signals generated and used according to present invention are shown in FIG. 1A, FIG. 2A, FIG. 3A, FIG. 4A and FIG. 7A and FIG. 8A. For the same bandwidth (100 kHz), the duration of the signals is only from 5 μs (FIG. 1A), if ¼ cycle titlet signal is used, up to 20 μs (FIG. 4A) for one cycle titlet.

Figure 8:
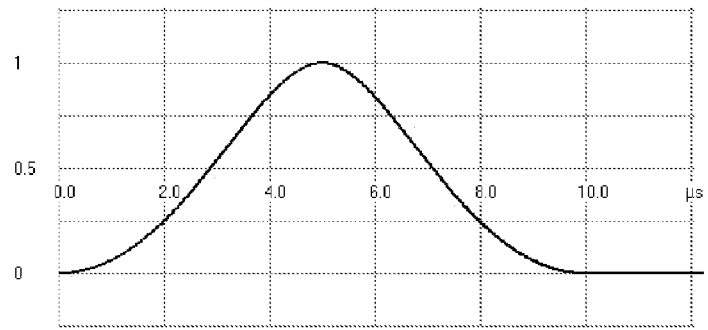
FIG. 8 describes a combinational sequence of two quarter-cycle titlet pulses—one up-wards and the other down-wards running frequencies (for both p=0.25); duration of the complex pulse is 10 μs, $f_2=100$ kHz (A), and the frequency distribution of a relative spectral density of this combinational pulse (B).
Figure 8:
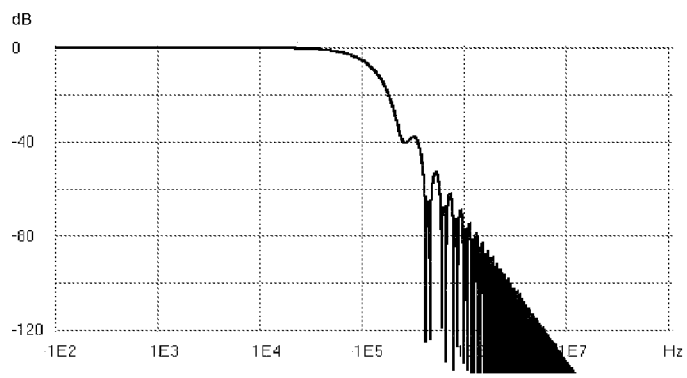
Figure 9:
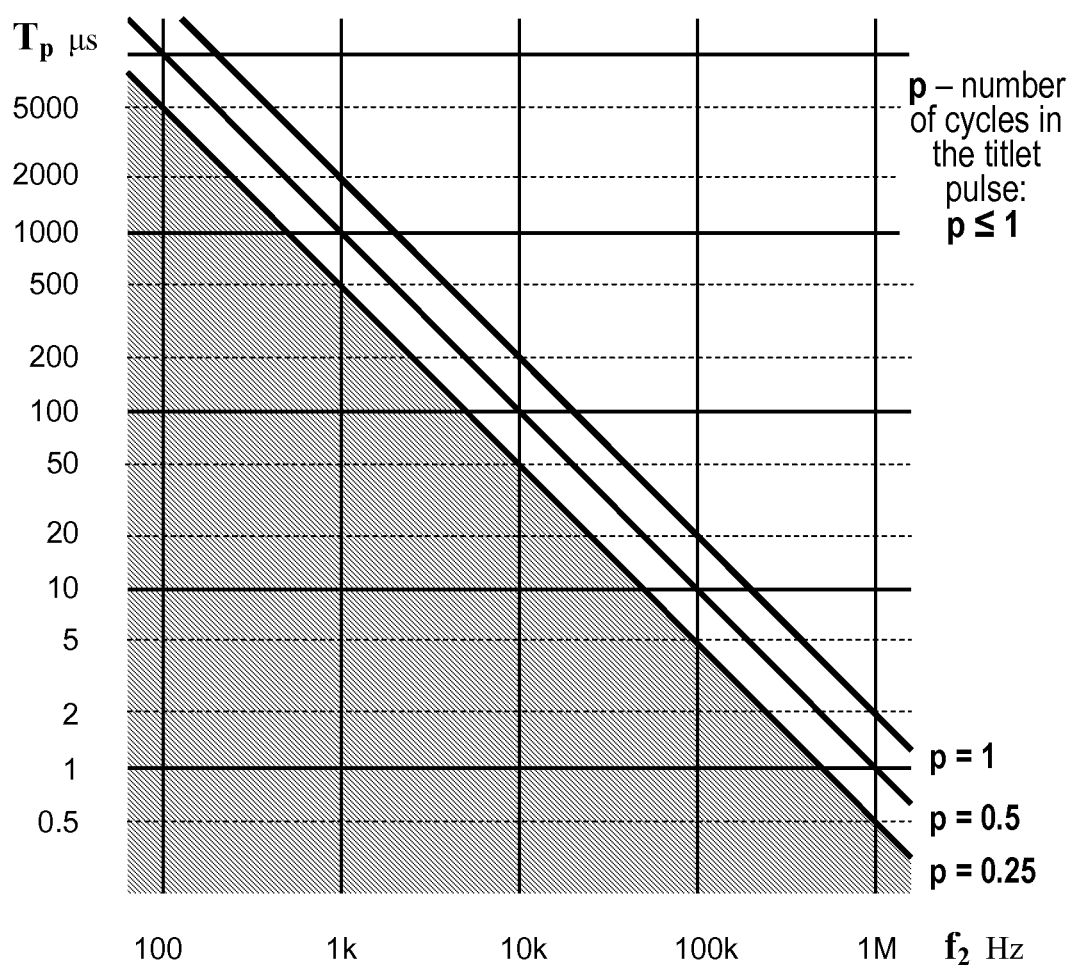
FIG. 9 is a nomogramme of the relationship between the titlet pulse duration $T_p$ and upper limit of the effective bandwidth $f_2$ for various values of the number of cycles p in the titlet pulse.
Figure 10:
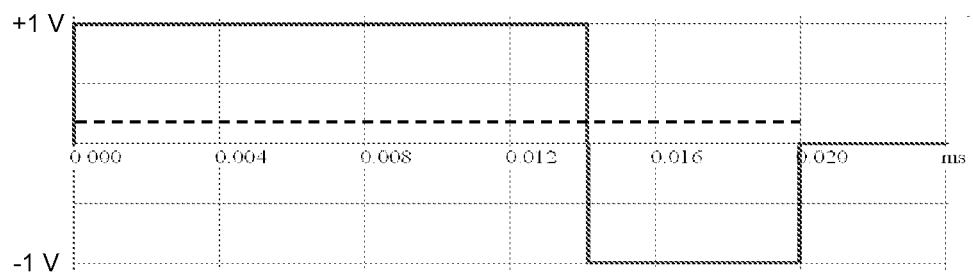
FIG. 10 is one cycle rectangular titlet pulse; according to the first example, the signal includes DC component equal to 0.207 V ($f_1=0$, $f_2=100$ kHz, $T=2/f_2=0.02$ ms, $T_1=T/2^{1/2}$).
Figure 11:
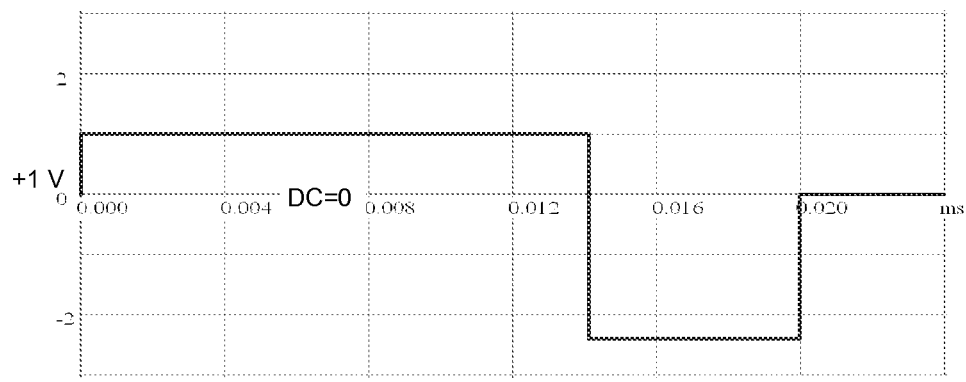
FIG. 11 is one cycle rectangular titlet pulse; according to second example the DC component of the signal is compensated ($f_2=100$ kHz $T=2/f_2=0.02$ ms, $T_1=T/2^{1/2}$, $A_1=1$, $A_2=-[1+sqrt(2)]=-2.4142$ V).
Figure 12:
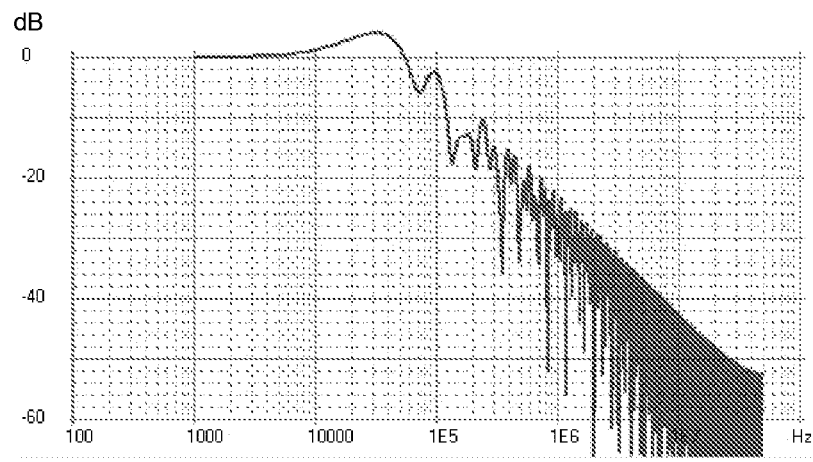
FIG. 12 is a spectrum of the one cycle rectangular titlet pulse shown in FIG. 10.
Figure 13:
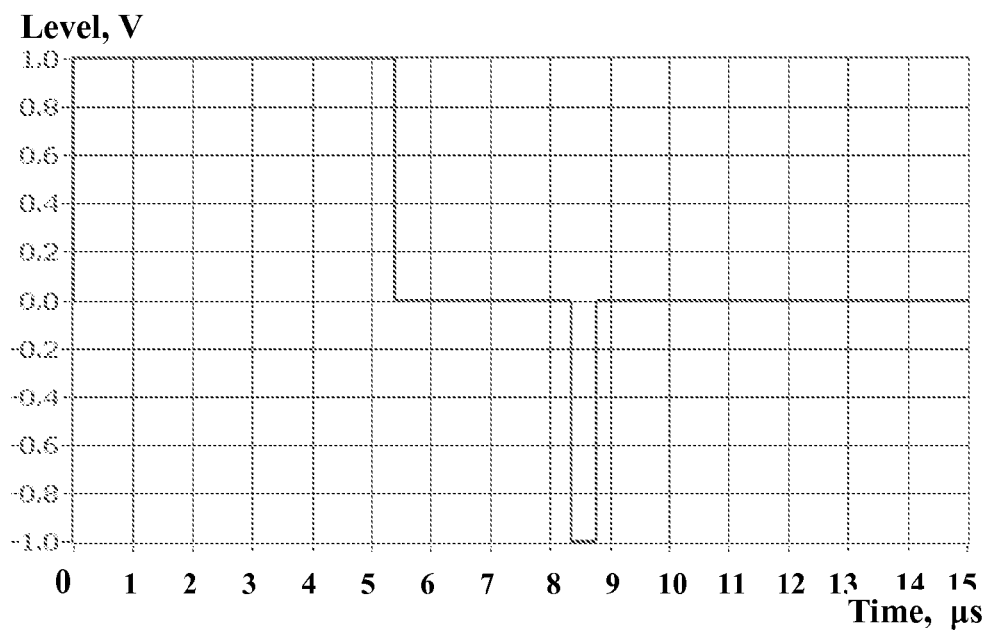
FIG. 13 describes a ternary (3-level) rectangular titlet pulse.
Figure 14:
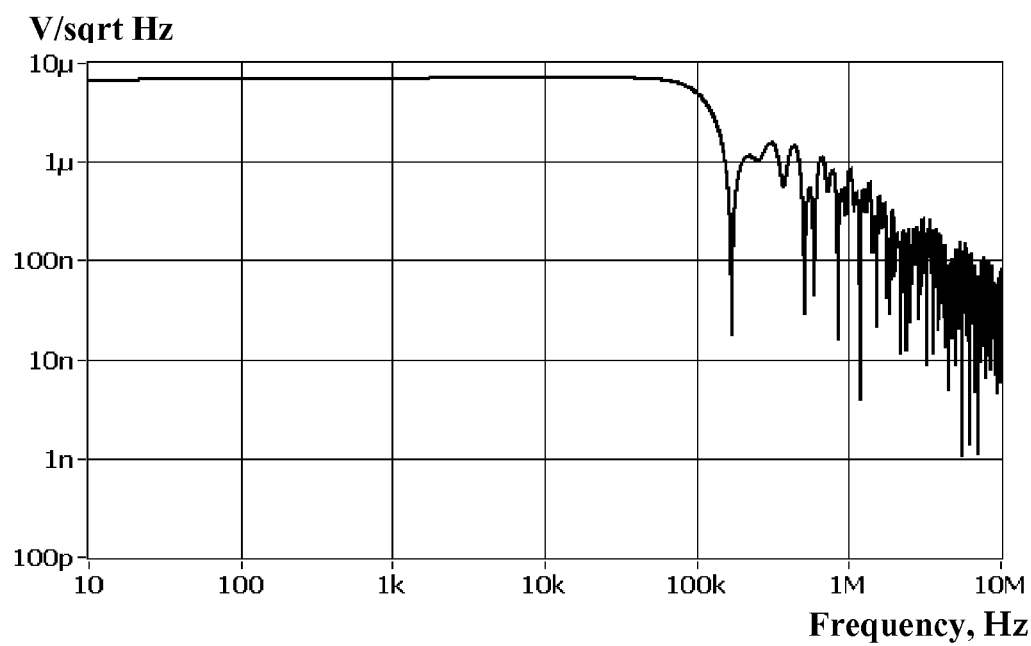
FIG. 14 depicts the spectral density distribution of rectangular titlet given in FIG. 13.
Figure 15:
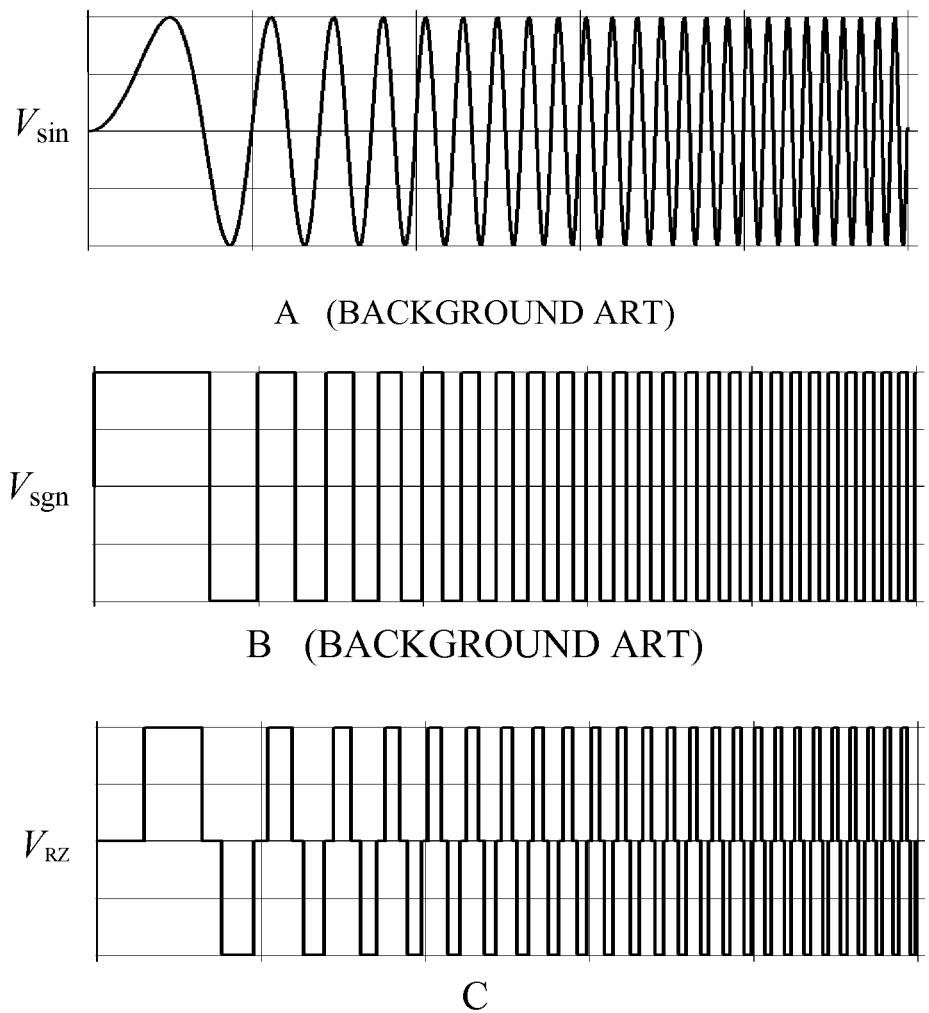
FIG. 15 shows diagrams of the sine wave chirp (A), rectangular non-return to zero (NRZ) or binary chirp (two-level) (B), and rectangular wave return-to-zero (RZ) chirp or ternary (three-level) chirp (C).
Figure 16:
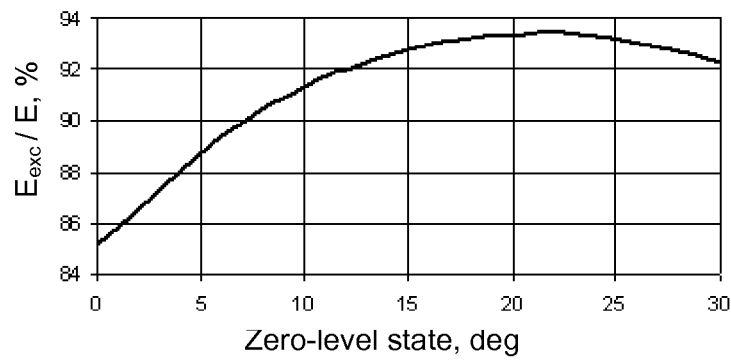
FIG. 16 is a dependence of the energy effectiveness $E_{exc}/E$ of the return to zero (RZ) rectangular wave ternary chirp on the duration of the zero-level state.

FIG. 8 is a nomogram of the relationship, valid between duration $T_p$ of the titlet pulse and upper limit $f_2$ of the effective bandwidth for various values of the number p of cycles in the titlet pulse.

Titlet pulses with linear frequency increase or decrease are used (FIG. 1A to FIG. 3A), but more preferable can be changing of frequency according to different functions, for example, according to exponential function as shown in FIG. 4A.

The signal shown on FIG. 7A is further modified by modulating the amplitude of the titlet pulse according to appropriate function, e.g., according to a power law $t^m$, where m is 8. In FIG. 8A is depicted a mirrored double titlet sequence consisting of up-word and downward quarter-cycle titlets. The spectrum in FIG. 8B shows outstanding quality—very good flatness, tail part reducing −60 dB per frequency decade, 90% of energy in the measurement bandwidth 100 kHz.

In general, the linear frequency titlet pulses in FIG. 1 to FIG. 8 can be described mathematically as $$A(t) = A \sin[2\pi(B/T) \cdot t^2/2] \quad (1)$$

where 0<t<Tp and the duration of one cycle titlet pulse is T=2/B, sec, during of which a rotation through 2π is covered. For a half-cycle titlet in FIG. 2A, the pulse duration Tp=T/2 and the final value for its phase is $\theta_{fin}=\pi$. The chirp rate B/T, Hz/s, corresponds to the excitation bandwidth B=100 kHz (FIG. 2B), which is covered by the said titlet pulse spectrum during one half-cycle Tp=T/2=10 μs of sine function (1). A bipolar titlet pulse with duration of one full-cycle Tp=T=20 μs is given in FIG. 3A, its RMS spectrum is shown in FIG. 3B.

The advantage of the invention is that the duration of titlet signal can be chosen discretely by quarter cycles k(π/2), where k=1, 2, 3, etc, wherein one full cycle of the titlet signal with duration T corresponds to 2π. The shortest titlet can last only a quarter of one cycle (k=1). In FIG. 1A is given an example of a quarter cycle (kθ$_{in}$=π/2) titlet with duration of Tp=5 μs. As the starting frequency in this example was chosen 1 kHz, the spectral density of the titlet pulse remains practically constant down to 1 kHz and even lower (see FIG. 1B). The tail part of the spectrum can be presented well by a first order asymptote (decreasing −20 dB/dec).

Excitation Energy and Impedance Dynamics

An outstanding property of both, chirp and titlet functions, is that the useful excitation bandwidth B can be set not dependent on duration $T_p$ of the titlet pulse when choosing appropriate frequency changing rate $B/T_p$ (1). In FIG. 5A is shown a short chirp consisting of 10 full cycles with duration Tp=10×T=200 μs, the significantly distorted RMS spectral density function of this signal is depicted in FIG. 5B. The spectrum of a long chirp in FIG. 6 ($10^5$ cycles, duration Tp=100000×T=2 s) shows practically no distortions.

Excitation energy depends proportionally on duration of the excitation pulse $T_p$. Therefore it is reasonable to use longer excitation pulses for obtaining better signal-to-noise ratio. But the main limiting factor is the speed of impedance variations (dynamics). For very fast variations, even so short excitation as the 10-cycle chirp (FIG. 5A, 200 μs), is not acceptable. Further shortening of chirp signals leads to serious distortions of their spectra. Introducing of well designed titlet pulses enables to solve the very high speed measurement problem.

Matching the needs for bandwidth, time, signal-to-noise ratio and dynamic requirements becomes into reality even in microsecond range duration impedance spectroscopy for application in lab-on-chip type analyzers and implantable and wearable medical devices.

Figure 19:
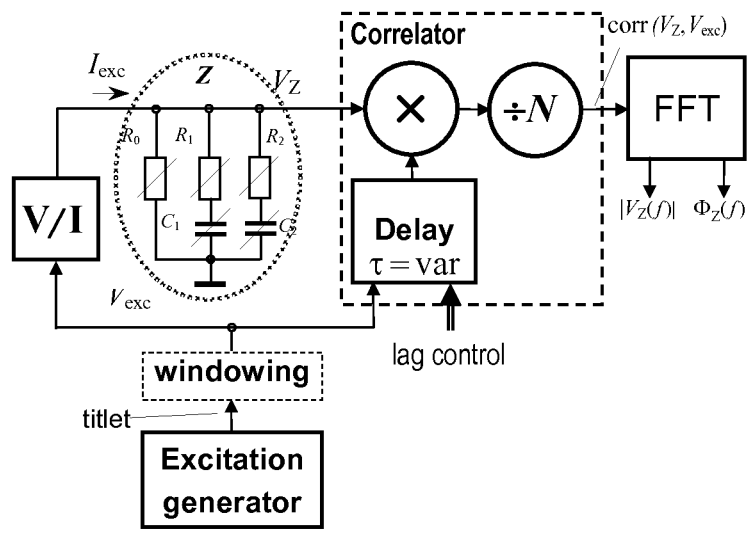
FIG. 19 is a block diagram of a hardwareoriented solution of the fast electrical bioimpedance spectrum measurement system with repeated measurement procedures for the case of low computing resources.

In FIG. 19, the generated titlet pulse, passed through an optional amplitude windowing, forms the excitation signal $V_{exc}$. Often, a boxcar-type trigonometric windowing (Tukey window) in time domain is used for shaping the spectrum (see FIG. 7). The test sample Z is stimulated by the current $I_{exc}(t)$ from a voltage-to-current converter V/I. Stimulating causes a response voltage $V_z(t)$, which is multiplied by a signal, which is shifted in phase in relation to the $V_{exc}$ at every instant of time separately, depending on the instant frequency of the titlet pulse. After averaging the results the cross-correlation function is $g_z(t)$ obtained. Fourier transform of the cross-correlation function gives the amplitude and phase spectra separately.

Figure 20:
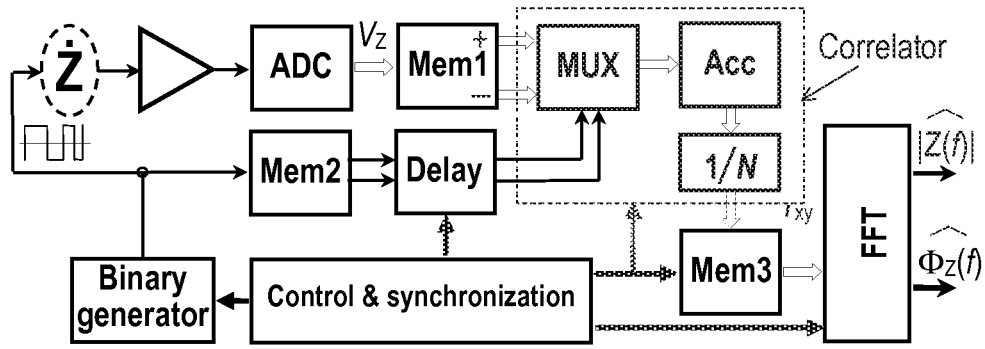
FIG. 20 is an extended block diagram of a hardware oriented solution of the fast electrical bioimpedance spectrum measurement system using binary excitation, in which the repeated measurement procedures are applied in case of low computing resources.

In FIG. 20, the basic structure of a practical evaluation unit is shown, including simplified correlation cell and memory blocks (Mem) for buffering of the response and other signals. Binary excitation is foreseen. Multiplying of the digitized response $V_z$ by the lagged binary (±1 level) excitation is accomplished by multiplexing (MUX) the inversed and non-inversed response values $V_z$ stored in the memory Mem1. The products are accumulated (Acc) and averaged for every lag step. The control and signal processing is performed by a FPGA (field programmable gate array) based processor unit.

Figure 21:
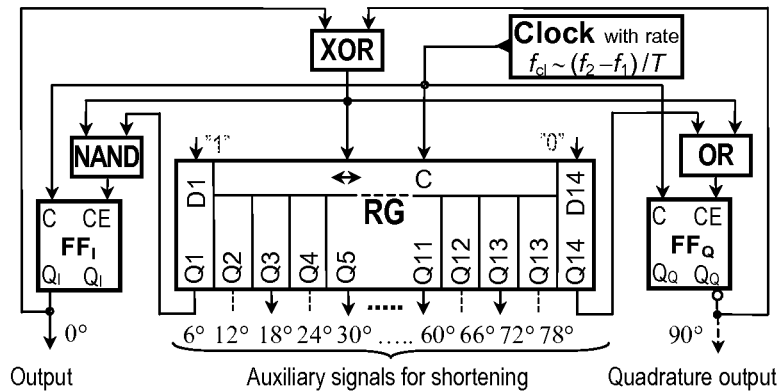
FIG. 21 is a reference circuitry for a digital generator of rectangular titlets. It contains a reversible shift register (stages Q1 to Q14), two flip-flops (FF1 and FF2) and some standard logic circuits as NAND, OR and XOR.

In practical experiments the trigger circuit with a central reversible shift register RG (FIG. 21) can be applied as a source of the binary excitation signals. This multi-use circuit can be simply commutated between the generating of NRZ or RZ chirp pulses with the 18° or 30° shortening. The instantaneous frequency of signal is determined by the changing clock rate.

The main advantage of the proposed method is the rapid estimation of complex spectrum of the impedance of biological objects in the wide range of frequencies. The method is also implementable in high throughput microfluidic laboratory-on-chip type devices for performing bioimpedance based joint time-frequency domain analysis of cells, cell cultures and droplets.

Figure 22:
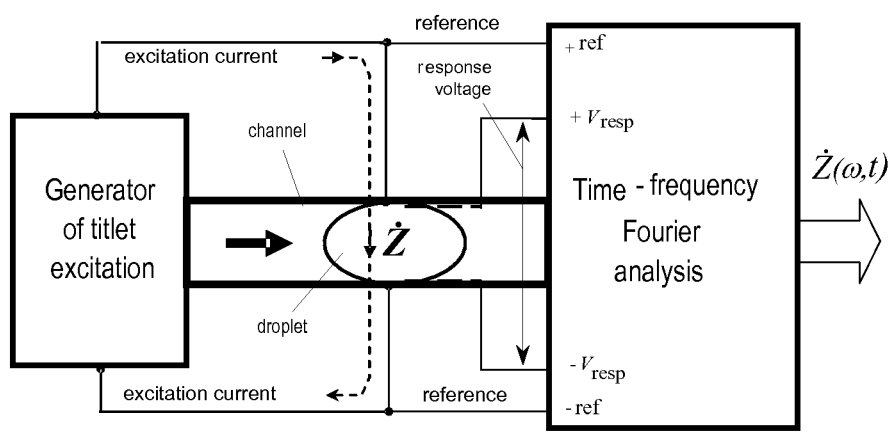
FIG. 22 is an experimental set-up for performing impedance spectroscopy of droplets and bioparticles in high-throughput microfluidic systems.

FIG. 22 describes a measurement set-up for impedance spectroscopy in microfluidic system. Microfluidic systems comprise a bio-mechanical part and an electronic part forming together a lab-on-a-chip type device. The electronic part generates droplet driving voltages and excitation signals for impedance measurement. It contains a generator of 100 μA level excitation current with rectangular titlet waveform. The excitation current flows through the droplet under study in a micrometer size microfluidic channel by the aid of current electrodes. The same signal forms also the reference signal for processing of the voltage response from voltage electrodes. A signal processing unit fulfils Fourier transform operations for performing the impedance spectroscopy for identifying the properties of cells in the droplet. The droplets will follow after about every 1-10 ms time interval in high-throughput systems. Therefore, the fast impedance measurement in a wide frequency range (e.g. from 1 kHz to 10 MHz) must be performed simultaneously and repeatedly at all the required frequencies within time interval less than 1 ms. Joint time-frequency Fourier transform gives a time dependent complex spectrum $Z(j\omega,t)$, known also as spectrogram.

Compared to the sine wave excitation, experiments with the rectangular wave titlets and chirps show close results without any significant degradation in measurement accuracy and repeatability of results. But the electronic part is much simpler and less power consuming because of operating only with discrete time 2- or 3-level (binary and ternary) pulse signals (see FIG. 10 to FIG. 14, and FIG. 15C).

What is claimed is:

1. A method for fast measurement of frequency response of an object having parameters, which are dynamically varying in time, the method comprising:
   determining a frequency range of interest, suitable for characterizing the object;
   determining a maximum measurement time, suitable for measuring the frequency response corresponding to the dynamically varying parameters of the object; and
   introducing into the object a titlet pulse, having a start frequency substantially in one end of the frequency range of interest and a stop frequency substantially in the other end of the frequency range of interest, and having a duration that is shorter or equal to the maximum measurement time, wherein a running frequency of the titlet pulse is changing from said start frequency to said stop frequency according to predetermined formula, wherein the number of cycles of the titlet pulse within the duration of the titlet pulse is one or less.

2. A method according to claim 1, wherein the number of the cycles is ½.

3. A method according to claim 1, wherein the number of the cycles is ¼.

4. A method according to claim 1, wherein the titlet pulse is based on sine wave function.

5. A method according to claim 1, wherein the titlet pulse is a rectangular wave return-to zero ternary signal, comprising a zero state section within each half-cycles of the signal.

6. A method according to claim 1, comprising generating more than one titlet pulse in sequence, thereby forming a complex excitation pulse with specifically designed power spectrum.

7. A method according to claim 6, wherein the complex excitation pulse comprises a first titlet with up-ward frequency and a second titlet with down-ward running frequencies.

8. A method according to claim 7, wherein both said first titlet and said second titlet contain 0.25, 0.5 or 1 cycles.

9. A method according to claim 5, wherein a duration of the zero state sections is from 15 to 30 degrees.

10. A method according to claim 1, wherein the running frequency of the titlet pulse is changing linearly from the start frequency to the stop frequency.

11. A method according to claim 1, wherein the running frequency of the titlet pulse is changed according to an exponential function $m^t$, where t is time and m is an arbitrary number.

12. A method according to claim 1, wherein the running frequency of the title pulse is changed according to a power law $t^m$, where t is time and m is an arbitrary number.

13. A method according to claim 1, wherein the running frequency of the titlet pulse is changed according to a logarithmic law $\log_m t$, where t is time and m is an arbitrary number.

14. A method according to claim 1, wherein the running frequency of the titlet pulse is changed according to a suitable arbitrary tabulated dependence on time moments depending on required shaping of the excitation spectrum.

15. A method according to claim 1, wherein the amplitude of the titlet pulse is modulated to achieve the most perfect fit of the shape of the power spectrum of titlet pulse to what is required by a measurement task.

16. A method according to claim 15, wherein the amplitude of the titlet pulse is changed according to a power function $t^m$, where t is time and m is an arbitrary number.

17. A method according to claim 5, wherein the rectangular signal is one cycle titlet pulse, duration of the cycle T of which is equal to stop frequency divided by 2 and the duration of the first half-cycle $T_1$ is $T/2^{1/2}$ and the duration $T_2$ of the second half-cycle is $T-T_1$.

18. A device for fast measurement of a frequency response of an object having parameters that are dynamically varying in time, the device comprising a source of excitation signal, said source adapted to generate a titlet pulse signal comprising ¼, ½ or 1 cycles within the duration of the titlet pulse, through said object; a signal processing unit, and a control unit, wherein an output of the source of excitation signal is connected to both an object and to a reference input of the signal processing unit, a signal input of which is connected to the output of object, where the control unit is adapted to form:
    the signal of start/stop of the measurement process, which is given to the start/stop inputs of the excitation source and the signal processing unit,
    the signal of chirp frequency control, which is given to the frequency control input of the excitation source, and
    the amplitude control signal, which is given to the amplitude control input of the excitation source.

19. A device according to claim 18, wherein the parameters of the excitation signal, including the start/stop interval, are calculated in the control unit from the predetermined values for the duration of the excitation signal and the start and stop frequencies or the bandwidth of the frequency change, and are used as the constants for forming/calculating the frequency control signal and the amplitude modulation signal.

* * * * *